(12) United States Patent
Liu et al.

(10) Patent No.: US 10,799,558 B2
(45) Date of Patent: Oct. 13, 2020

(54) USE OF CD24 PROTEINS FOR TREATING LEPTIN-DEFICIENT CONDITIONS

(71) Applicant: ONCOIMMUNE, INC., Rockville, MD (US)

(72) Inventors: Yang Liu, Washington, DC (US); Pan Zheng, Washington, DC (US); Martin Devenport, Gaithersburg, MD (US)

(73) Assignee: ONCOIMMUNE, INC., Rockville, MD (US)

( * ) Notice: Subject to any disclaimer, the term of this patent is extended or adjusted under 35 U.S.C. 154(b) by 48 days.

(21) Appl. No.: 16/074,726

(22) PCT Filed: Feb. 2, 2017

(86) PCT No.: PCT/US2017/016120
§ 371 (c)(1),
(2) Date: Aug. 1, 2018

(87) PCT Pub. No.: WO2017/136492
PCT Pub. Date: Aug. 10, 2017

(65) Prior Publication Data
US 2019/0038716 A1 Feb. 7, 2019

Related U.S. Application Data

(60) Provisional application No. 62/290,202, filed on Feb. 2, 2016.

(51) Int. Cl.
| | | |
|---|---|---|
| *A61K 38/17* | (2006.01) | |
| *A61P 5/00* | (2006.01) | |
| *A61K 47/68* | (2017.01) | |
| *A61K 38/22* | (2006.01) | |

(52) U.S. Cl.
CPC ...... *A61K 38/1774* (2013.01); *A61K 38/2264* (2013.01); *A61K 47/6801* (2017.08); *A61P 5/00* (2018.01)

(58) Field of Classification Search
None
See application file for complete search history.

(56) References Cited

U.S. PATENT DOCUMENTS

| | | | |
|---|---|---|---|
| 8,808,697 B2 * | 8/2014 | Zheng | A61K 38/177 424/134.1 |
| 2013/0136739 A1 | 5/2013 | Zheng et al. | |
| 2014/0294774 A1 | 10/2014 | Nieuwdorp et al. | |
| 2015/0272980 A1 | 10/2015 | Rodrigueza et al. | |

OTHER PUBLICATIONS

Tsoukas et al. (Metabolism 2015, p. 47-59 ).*
Bokarewa (Ann Rheum Dis, 2003, p. 952-956).*
McLean et al. (Molecular Immunology, 2000, p. 837-845).*
GenBank CAC20454.1, 2000.*
Fairbridge, N.A., et al., "Loss of CD24 in Mice Leads to Metabolic Dysfunctions and a Reduction in White Adipocyte Tissue," PLOS One, vol. 10, No. 11, (Nov. 4, 2015).
International Search Report of PCT/US2017/016120 dated Jun. 21, 2017.
Written Opinion of PCT/US2017/016120 dated Jun. 21, 2017.

* cited by examiner

*Primary Examiner* — Agnieszka Boesen
(74) *Attorney, Agent, or Firm* — Polsinelli PC; Ron Galant

(57) ABSTRACT

This invention relates to the use of a CD24 protein for treating leptin-deficient conditions, such as lipodystrophy, by increasing the level of circulating leptin.

19 Claims, 2 Drawing Sheets

Specification includes a Sequence Listing.

FIG. 1A

MGRAMVARLGLGLLLLALLLPTQIYSSETTTGTSSNSSQSTSNSGLAP
NPTNATTKPKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIG. 1B

MGRAMVARLGLGLLLLALLLPTQIYSSETTTGTSSNSSQSTSNSGLAP
NPTNATTKVPKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 1C

MGRAMVARLGLGLLLLALLLPTQIYSSETTTGTSSNSSQSTSNSGLAP
NPTNATTKAPKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

SEQUENCE LISTING

```
<160> NUMBER OF SEQ ID NOS: 12

<210> SEQ ID NO 1
<211> LENGTH: 31
<212> TYPE: PRT
<213> ORGANISM: Homo sapiens
<220> FEATURE:
<221> NAME/KEY: VARIANT
<222> LOCATION: (31)...(31)
<223> OTHER INFORMATION: Valine or Alanine

<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 2
<211> LENGTH: 30
<212> TYPE: PRT
<213> ORGANISM: Homo sapiens

<400> SEQUENCE: 2

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 3
<211> LENGTH: 27
<212> TYPE: PRT
<213> ORGANISM: Mus musculus

<400> SEQUENCE: 3

Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
```

```
                    20                  25

<210> SEQ ID NO 4
<211> LENGTH: 26
<212> TYPE: PRT
<213> ORGANISM: Homo sapiens

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Ser
                20                  25

<210> SEQ ID NO 5
<211> LENGTH: 287
<212> TYPE: PRT
<213> ORGANISM: Artificial
<220> FEATURE:
<223> OTHER INFORMATION: Fusion protein

<400> SEQUENCE: 5

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Pro Lys Ser Cys Asp Lys Thr His
        50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
        275                 280                 285
```

<210> SEQ ID NO 6
<211> LENGTH: 261
<212> TYPE: PRT
<213> ORGANISM: Artificial
<220> FEATURE:
<223> OTHER INFORMATION: Fusion protein

<400> SEQUENCE: 6

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 7
<211> LENGTH: 231
<212> TYPE: PRT
<213> ORGANISM: Homo sapiens

<400> SEQUENCE: 7

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

```
Asp Val Ser His Glu Asp Pro Glu Val Lys Phe Asn Trp Tyr Val Asp
 50                 55                  60
Gly Val Glu Val His Asn Ala Lys Thr Lys Pro Arg Glu Glu Gln Tyr
 65                  70                  75                  80
Asn Ser Thr Tyr Arg Val Val Ser Val Leu Thr Val Leu His Gln Asp
                 85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Asp Glu Leu Thr Lys
130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
210                 215                 220
Leu Ser Leu Ser Pro Gly Lys
225                 230

<210> SEQ ID NO 8
<211> LENGTH: 288
<212> TYPE: PRT
<213> ORGANISM: Artificial
<220> FEATURE:
<223> OTHER INFORMATION: Fusion protein

<400> SEQUENCE: 8

Met Gly Arg Ala Met Val Ala Arg Leu Gly Leu Gly Leu Leu Leu Leu
 1               5                  10                  15
Ala Leu Leu Leu Pro Thr Gln Ile Tyr Ser Ser Glu Thr Thr Thr Gly
                 20                  25                  30
Thr Ser Ser Asn Ser Ser Gln Ser Thr Ser Asn Ser Gly Leu Ala Pro
             35                  40                  45
Asn Pro Thr Asn Ala Thr Thr Lys Val Pro Lys Ser Cys Asp Lys Thr
 50                  55                  60
His Thr Cys Pro Pro Cys Pro Ala Pro Glu Leu Leu Gly Gly Pro Ser
 65                  70                  75                  80
Val Phe Leu Phe Pro Pro Lys Pro Lys Asp Thr Leu Met Ile Ser Arg
                 85                  90                  95
Thr Pro Glu Val Thr Cys Val Val Val Asp Val Ser His Glu Asp Pro
            100                 105                 110
Glu Val Lys Phe Asn Trp Tyr Val Asp Gly Val Glu Val His Asn Ala
        115                 120                 125
Lys Thr Lys Pro Arg Glu Glu Gln Tyr Asn Ser Thr Tyr Arg Val Val
130                 135                 140
Ser Val Leu Thr Val Leu His Gln Asp Trp Leu Asn Gly Lys Glu Tyr
145                 150                 155                 160
Lys Cys Lys Val Ser Asn Lys Ala Leu Pro Ala Pro Ile Glu Lys Thr
                165                 170                 175
```

Ile Ser Lys Ala Lys Gly Gln Pro Arg Glu Pro Gln Val Tyr Thr Leu
             180                 185                 190

Pro Pro Ser Arg Asp Glu Leu Thr Lys Asn Gln Val Ser Leu Thr Cys
         195                 200                 205

Leu Val Lys Gly Phe Tyr Pro Ser Asp Ile Ala Val Glu Trp Glu Ser
     210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                 245                 250                 255

Arg Trp Gln Gln Gly Asn Val Phe Ser Cys Ser Val Met His Glu Ala
             260                 265                 270

Leu His Asn His Tyr Thr Gln Lys Ser Leu Ser Leu Ser Pro Gly Lys
         275                 280                 285

<210> SEQ ID NO 9
<211> LENGTH: 288
<212> TYPE: PRT
<213> ORGANISM: Artificial
<220> FEATURE:
<223> OTHER INFORMATION: Fusion protein

<400> SEQUENCE: 9

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
             20                  25                  30

Thr Ser Ser Asn Ser Ser Gln Ser Thr Ser Asn Ser Gly Leu Ala Pro
         35                  40                  45

Asn Pro Thr Asn Ala Thr Thr Lys Ala Pro Lys Ser Cys Asp Lys Thr
50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                 85                  90                  95

Thr Pro Glu Val Thr Cys Val Val Val Asp Val Ser His Glu Asp Pro
             100                 105                 110

Glu Val Lys Phe Asn Trp Tyr Val Asp Gly Val Glu Val His Asn Ala
         115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                 165                 170                 175

Ile Ser Lys Ala Lys Gly Gln Pro Arg Glu Pro Gln Val Tyr Thr Leu
             180                 185                 190

Pro Pro Ser Arg Asp Glu Leu Thr Lys Asn Gln Val Ser Leu Thr Cys
         195                 200                 205

Leu Val Lys Gly Phe Tyr Pro Ser Asp Ile Ala Val Glu Trp Glu Ser
     210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                 245                 250                 255

```
Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
            275                 280                 285
```

<210> SEQ ID NO 10
<211> LENGTH: 29
<212> TYPE: PRT
<213> ORGANISM: Macaca fascicularis

<400> SEQUENCE: 10

```
Thr Val Thr Thr Ser Ala Pro Leu Ser Ser Asn Ser Pro Gln Asn Thr
1               5                   10                  15

Ser Thr Thr Pro Asn Pro Ala Asn Thr Thr Lys Ala
            20                  25
```

<210> SEQ ID NO 11
<211> LENGTH: 262
<212> TYPE: PRT
<213> ORGANISM: Artificial
<220> FEATURE:
<223> OTHER INFORMATION: Fusion protein

<400> SEQUENCE: 11

```
Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Val Pro
            20                  25                  30

Lys Ser Cys Asp Lys Thr His Thr Cys Pro Pro Cys Pro Ala Pro Glu
            35                  40                  45

Leu Leu Gly Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
```

```
<210> SEQ ID NO 12
<211> LENGTH: 262
<212> TYPE: PRT
<213> ORGANISM: Artificial
<220> FEATURE:
<223> OTHER INFORMATION: Fusion protein

<400> SEQUENCE: 12

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Ala Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260
```

USE OF CD24 PROTEINS FOR TREATING LEPTIN-DEFICIENT CONDITIONS

FIELD OF THE INVENTION

The present invention relates to CD24 proteins for use in treating leptin-deficient conditions.

BACKGROUND

Leptin-deficient conditions such as leptin deficiency due to mutations in the leptin gene, hypothalamic amenorrhea, and lipodystrophy syndromes (LS), are characterized by partial or complete absence of adipose tissue and hormones derived from adipose tissue, most importantly leptin (Rodriguez et al 2015). In those disorders, the subcutaneous adipose tissue is the most affected and fat accumulates in non-adipose tissues. Lipoatrophy, is a more specific term used when describing the loss of fat from one area (usually the face). Patients deficient in leptin exhibit a number of severe metabolic abnormalities such as hyperglycemia, hypertriglyceridemia, and hepatic steatosis, which can progress to diabetes mellitus, acute pancreatitis, and hepatic cirrhosis, respectively. Lipodystrophy may also lead to osteosclerosis.

Generalized lipodystrophy is the most striking form of lipodystrophy and can be either acquired or congenital. Acquired lipodystrophy may develop from the use of highly active retroviral therapy (HAART) or underlying HIV infection (the most common form of lipodystrophy) or autoimmune conditions. The pathogenesis of congenital forms of lipodystrophy is determined by molecular deficiencies in several genes that orchestrate adipocyte differentiation, lipid droplet morphology, and lipid metabolism.

The clinical manifestations of LS are essentially determined by the partial or complete lack of white adipose tissue, leading to low or undetectable levels of the adipose-derived cytokine leptin. Leptin is previously known as an adipocytokine that regulates several metabolic processes including glucose homeostasis, insulin sensitivity, and fatty acid oxidation. The state of leptin deficiency seen in lipodystrophy leads to the development of several metabolic abnormalities and approximately 80% of the patients with lipodystrophy fulfill the diagnostic criteria for metabolic syndrome.

Current approved methods of treatment for leptin-deficient conditions like lipodystrophy involve leptin replacement therapy (LRT), such as with the leptin analog metreleptin (MYALEPT). However, LRT is associated with risks related to the development of neutralizing anti-drug antibodies and lymphoma, and it is currently approved only for cases of generalized non-HIV lipodystrophy. Furthermore, due to its low half-life, metreleptin must be administered once or twice daily (usually at the same time of day) to mimic the natural leptin circadian cycle. Therefore, there is a need for alternative methods of treating LS and leptin-deficiencies, particularly for patients with HIV.

SUMMARY OF THE INVENTION

This invention describes a novel method for treating leptin-deficient conditions in a subject by administering a CD24 protein to a subject in need thereof. Also provided is a method for treating or preventing treating lipodystrophy in patients with HIV by administering the CD24 protein to a subject in need thereof.

The CD24 protein may comprise the sequence of mature human CD24 or a variant thereof. The mature human CD24 may comprise the sequence of SEQ ID NO: 1 or 2. The CD24 protein may comprise any or all of the extracellular domain of human CD24. The CD24 protein may comprise the signal sequence of SEQ ID NO: 4 to allow secretion from a cell expressing the protein. The signal peptide sequence may be one that is found on other transmembrane or secreted proteins, or one modified from the existing signal peptides known in the art. The CD24 protein may be soluble and/or may be glycosylated. The CD24 protein may be produced using a eukaryotic protein expression system, which may comprise a vector contained in a Chinese Hamster Ovary cell line or a replication-defective retroviral vector. The replication defective retroviral vector may be stably integrated into the genome of a eukaryotic cell.

The CD24 protein may comprise a protein tag, which may be fused at the N- or C-terminus of the CD24 protein. The protein may comprise a portion of a mammalian immunoglobulin (Ig), which may be the Fc portion of a human Ig protein. The human Ig protein may comprise the hinge region and CH2 and CH3 domains of the human Ig protein, and the human Ig protein may be IgG1, IgG2, IgG3, IgG4, or IgA. The Fc portion may also comprise the hinge region and CH3 and CH4 domains of IgM. The CD24 protein may comprise the sequence of SEQ ID NO: 5, 6, 8 or 9.

BRIEF DESCRIPTION OF THE DRAWINGS

FIG. 1A shows the amino acid composition of the full length CD24 fusion protein, CD24IgG1Fc (also referred to herein as CD24Fc) (SEQ ID NO: 5). The underlined 26 amino acids are the signal peptide of CD24 (SEQ ID NO: 4), which are cleaved off during secretion from a cell expressing the protein and thus missing from the mature version of the protein (SEQ ID NO: 6). The bold portion of the sequence is the extracellular domain of the mature CD24 protein used in the fusion protein (SEQ ID NO: 2). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 7). FIG. 1B shows the sequence of CD24$^V$Fc (SEQ ID NO: 8), in which the mature human CD24 protein (bold) is the valine polymorphic variant of SEQ ID NO: 1. FIG. 1C shows the sequence of CD24$^A$Fc (SEQ ID NO: 9), in which the mature human CD24 protein (bold) is the alanine polymorphic variant of SEQ ID NO: 1. The various parts of the fusion protein in FIGS. 1B and 1C are marked as in FIG. 1A and the variant valine/alanine amino acid is double underlined.

DETAILED DESCRIPTION

Figure 2:
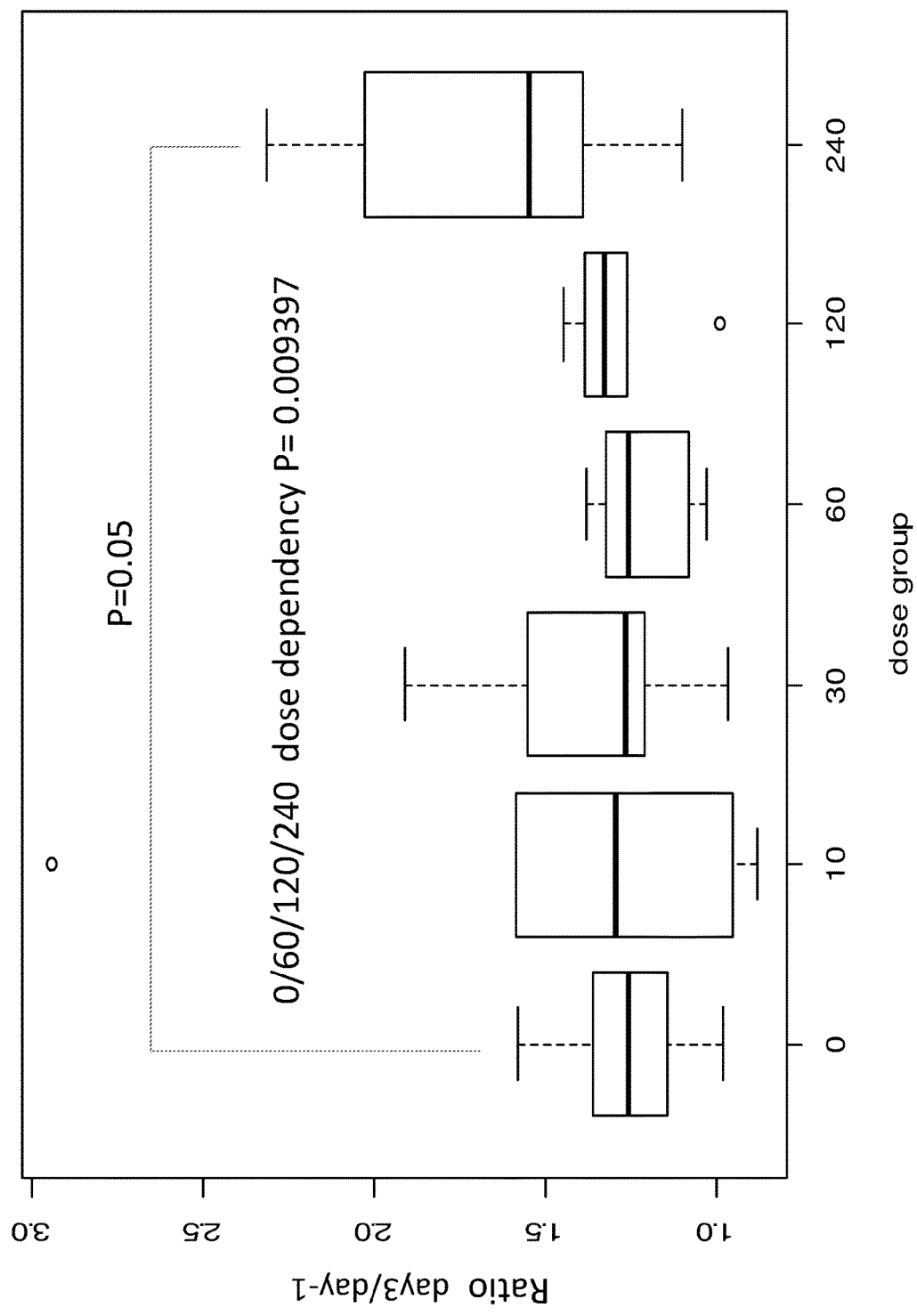
FIG. 2 shows the ratio of leptin in the serum of healthy human subjects at day 3 post CD24Fc treatment compared to day −1 pre-treatment. The drug was administered on day 0. The data is represented by CD24Fc dosing cohort; the 0 mg/kg group represents the placebo control group.

Here we describe the surprising discovery that the administration of a CD24 protein to human subjects causes an increase in the circulating levels of leptin within the blood. This is useful for the treatment of leptin-deficient conditions, such as lipodystrophy, by increasing the level of circulating leptin. In a specific embodiment the invention relates to methods of treating lipodystrophy in patients with HIV.

As described in more detail herein, CD24 is a small glycosyl-phosphatidyl-inositol (GPI)-anchored glycoprotein with widespread expression among both hematopoietic and non-hematopoietic cells, which is encoded by a coding sequence of 240 base pairs. Of the 80 amino acids, the first 26 constitute the signal peptide, while the last 23 serve as a signal for cleavage to allow for the attachment of the GPI tail. As a result, the mature human CD24 molecule has only 31 amino acids. Of the 31 amino acids in the mature CD24 protein, the last (C-terminal) amino acid is polymorphic among the human population. A C to T transition at nucleotide 226 results in the substitution of alanine (a) with valine (v). Since this residue is immediately N-terminal to the cleavage site, and since the replacement is non-conservative, these two alleles may be expressed at different efficiencies on the cell surface.

CD24 is known to be a genetic modifier for multiple sclerosis (MS), rheumatoid arthritis (RA), and systemic lupus erythematosus (SLE). At the population level, the $CD24^{v/v}$ genotype is more than twice as frequent as it is in the normal population. Among multiplex MS families, the $CD24^{v}$ allele is preferentially transmitted to the MS patients in comparison to healthy controls. Furthermore, among the MS patients who have a more severe form of the disease (Expanded Disability Status Scale [EDSS] at or exceeding 6.0, when the patients lose the ability to walk independently), $CD24^{v/v}$ individuals took, on average, 7 years to reach EDSS 6.0 from the first clinical symptom, yet the $CD24^{a/v}$ or $CD24^{a/a}$ individuals reached EDSS 6.0 in 13 to 15 years. Conversely, a dinucleotide deletion in the 3' untranslated region of CD24 messenger ribonucleic acid (mRNA), which reduces CD24 mRNA stability and thus reduces CD24 expression, protects humans against MS and other autoimmune diseases. To date, CD24 has not been shown to affect lipid levels.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of a human or an animal from a disease, means preventing, suppressing, repressing, or completely eliminating the disease. Preventing the disease involves administering a composition of the present invention to a human or an animal prior to onset of the disease. Suppressing the disease involves administering a composition of the present invention to a human or an animal after induction of the disease but before its clinical appearance. Repressing the disease involves administering a composition of the present invention to a human or an animal after clinical appearance of the disease.

A "variant" may mean a peptide or polypeptide that differs in amino acid sequence by the insertion, deletion, or conservative substitution of amino acids, but retain some biological activity. Representative examples of "biological activity" for CD24 include the ability to bind to a lectin, in particular, Siglecs (Sialic acid-binding immunoglobulin-type lectins), and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may comprise the amino acid sequence of mature human CD24 or those from other mammals, which corresponds to the extracellular domain (ECD), or a variant thereof. As described above, the sequence of the mature human CD24 protein is 31 amino acids long with a variable alanine (a) with valine (v) residue at its C-terminal end:

(SEQ ID NO: 1)
SETTTGTSSNSSQSTSNSGLAPNPTNATTK(V/A)

The C-terminal valine or alanine may be immunogenic and may be omitted from the CD24 protein to reduce its immunogenicity. Therefore, in another embodiment, the CD24 protein may comprise the amino acid sequence or mature human CD24 lacking the C-terminal amino acid:

SETTTGTSSNSSQSTSNSGLAPNPTNATTK (SEQ ID NO: 2)

Despite considerable sequence variations in the amino acid sequence of the mature CD24 proteins from mouse and human, they are functionally equivalent as human CD24Fc has been shown to be active in the mouse. The amino acid sequence of the human CD24 ECD shows some sequence conservation with the mouse protein (39% identity; Genbank accession number NP_033976). However, it is not that surprising that the percent identity is not higher as the CD24 ECD is only 27-31 amino acids in length depending on the species, and binding to some of its receptor(s), such as Siglec 10/G, is mediated by its sialic acid and/or galactose sugars of the glycoprotein. The amino acid sequence identity between the extracellular domains of the human Siglec-10 (GenBank accession number AF310233) and its murine homolog Siglec-G (GenBank accession number NP_766488) receptor proteins is 63%. As a result of sequence conservation between mouse and human CD24 primarily in the C-terminus and in the abundance of glycosylation sites, significant variations in the mature CD24 proteins may be tolerated in using the CD24 protein, especially if those variations do not affect the conserved residues in the C-terminus or do not affect the glycosylation sites from either mouse or human CD24. Therefore, the CD24 protein may comprise the amino acid sequence of mature murine CD24:

NQTSVAPFPGNQNISASPNPTNATTRG. (SEQ ID NO: 3)

The amino acid sequence of the human CD24 ECD shows more sequence conservation with the cynomolgus monkey protein (52% identity; UniProt accession number UniProtKB-I7GKK1) than with mouse. Again, this is not surprising given that the percent identity is not higher as the ECD is only 29-31 amino acids in length in these species, and the role of sugar residues in binding to its receptor(s). The amino acid sequence of cynomolgus Siglec-10 receptor has not been determined but the amino acid sequence identity between the human and rhesus monkey Siglec-10 (GenBank accession number XP_001116352) proteins is 89%. Therefore, the CD24 protein may also comprise the amino acid sequence of mature cynomolgous (or rhesus) monkey CD24:

TVTTSAPLSSNSPQNTSTTPNPANTTTKA (SEQ ID NO: 10)

The CD24 protein may be soluble. The CD24 protein may further comprise an N-terminal signal peptide, to allow secretion from a cell expressing the protein. The signal peptide sequence may comprise the amino acid sequence MGRAMVARLGLGLLLLALLLPTQIYS (SEQ ID NO: 4), which is from the endogenous human CD24 signal peptide. Alternatively, the signal sequence may be any of those that are found on other transmembrane or secreted proteins, or those modified from the existing signal peptides known in the art.

a. Fusion

The CD24 protein may be fused at its N- or C-terminal end to a protein tag, which may comprise a portion of a mammalian Ig protein, which may be human or mouse. The portion may comprise an Fc region of the Ig protein. The Fc region may comprise the hinge region and CH2 and CH3 domains of the Ig protein. The Ig protein may be human IgG1, IgG2, IgG3, IgG4, IgM, or IgA. The Fc portion may comprise the human immunoglobulin G1 (IgG1) isotype SEQ ID NO: 7. The Ig protein may also be IgM, and the Fc portion may comprise the hinge region and CH3 and CH4 domains of IgM. The protein tag may also comprise GST, His, or FLAG. Methods for making fusion proteins and purifying fusion proteins are well known in the art.

Based on our preclinical research, for the construction of the fusion protein CD24Fc identified in the examples, we have chosen to use the truncated form of native CD24 molecule of 30 amino acids which lacks the final polymorphic amino acid before the GPI signal cleavage site (SEQ ID NO: 2). This protein is fused to a human IgG1 Fc domain (SEQ ID NO: 7). The full length CD24Fc fusion protein is provided in SEQ ID NO: 5 (FIG. 1) and the mature version of CD24Fc fusion protein that is secreted from the cell (i.e. lacking the signal sequence which is cleaved off) is provided in SEQ ID NO: 6. Processed polymorphic variants of mature CD24 (that is, mature CD24 protein having SEQ ID NO: 1) fused to IgG1 Fc may comprise SEQ ID NO: 11 or 12.

b. Production

The CD24 proteins described herein may be heavily glycosylated, and the sugar moieties may be involved in the biological activity of CD24, such as immune cell costimulation, interaction with Siglecs (Sialic acid-binding immunoglobulin-type lectins) and interaction with a damage-associated molecular pattern molecule (DAMP). The CD24 protein may be prepared using a eukaryotic expression system. The expression system may entail expression from a vector in mammalian cells, such as Chinese Hamster Ovary (CHO) cells. The system may also be a viral vector, such as a replication defective retroviral vector that may be used to infect eukaryotic cells. The CD24 protein may also be produced from a stable cell line that expresses the CD24 protein from a vector or a portion of a vector that has been integrated into the cellular genome. The stable cell line may express the CD24 protein from an integrated replication-defective retroviral vector. The expression system may be GPEx™.

c. Pharmaceutical Composition

The CD24 proteins described herein may be contained in a pharmaceutical composition, which may comprise at least one pharmaceutically acceptable excipient. The pharmaceutical composition may comprise a solvent, which may keep the CD24 protein stable over an extended period. The solvent may be PBS, which may keep the CD24 protein stable for at least 66 months at about −20° C. (−15 to −25° C.). The solvent may be capable of accommodating the CD24 protein in combination with another drug.

d. Dosage

The dose of the CD24 protein may ultimately be determined through a clinical trial to determine a dose with acceptable toxicity and clinical efficacy. The initial clinical dose may be estimated through pharmacokinetics and toxicity studies in rodents and non-human primates. The dose of the CD24 protein may be 0.01 mg/kg to 1000 mg/Kg, and may be 1 to 500 mg/kg, depending on the desired amount of leptin increase and the route of administration. The CD24 protein may be administered by intravenous infusion or subcutaneous or intramural injection, and the dose may be 10-100,000 mg, 10-10,000 mg, 10-1000 mg, 10-500 mg, 10-240 mg, 10-120 mg, or 10, 30, 60, 120, or 240 mg, where the subject is a human.

3. Methods of Treatment

The CD24 protein may be administered to a subject in need of increasing leptin levels, such as those with a leptin-deficient conditions such as leptin deficiency due to hypomorphic mutations or epigenetic silencing in the leptin gene, hypothalamic amenorrhea, and lipodystrophy syndromes (LS), including lipoatrophy. Furthermore, the subject may have generalized lipodystrophy that is either acquired or congenital. Acquired lipodystrophy includes those subjects using highly active retroviral therapy (HAART) or those with an underlying HIV infection (the most common form of lipodystrophy) or autoimmune conditions. Congenital lipodystrophy includes those subjects with a molecular deficiency in any of several genes that orchestrate adipocyte differentiation, lipid droplet morphology, and lipid metabolism. The subject may be a mammal such as a human.

The subject may have been previously treated with a leptin replacing drug, such as leptin replacement therapy (LRT), or a drug that increases leptin levels in the blood. A specific example of an LRT therapy is the leptin analog metreleptin (Myalept, Aegerion Pharmaceuticals, Inc., Cambridge, Mass., USA).

a. Administration

The route of administration of the pharmaceutical composition may be parenteral. Parenteral administration includes, but is not limited to, intravenous, intraarterial, intraperitoneal, subcutaneous, intramuscular, intrathecal, intraarticular and direct injection into affected joints. For veterinary use, the agent may be administered as a suitably acceptable formulation in accordance with normal veterinary practice. The veterinarian can readily determine the dosing regimen and route of administration that is most appropriate for a particular animal. The pharmaceutical composition may be administered to a human patient, cat, dog, large animal, or an avian.

The CD24 protein may be administered simultaneously or metronomically with other treatments. The term "simultaneous" or "simultaneously" as used herein, means that the CD24 protein and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 protein may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The CD24 protein may be administered at any point prior to a second treatment of the CD24 protein including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The CD24 protein may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 protein may be administered at any point prior after a previous CD24 treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

b. Combination Treatment

The CD24 protein may be combined with another drug or treatment regimen, such as leptin replacement therapy (LRT), or a drug that increases leptin levels in the blood. A specific example of an LRT therapy is the leptin analog metreleptin (Myalept, Aegerion Pharmaceuticals, Inc., Cambridge, Mass., USA). The CD24 protein and the other drug may be administrated together or sequentially.

The present invention has multiple aspects, illustrated by the following non-limiting examples.

EXAMPLES

Example 1

This example demonstrates that CD24Fc increases circulating leptin levels. Changes of leptin in plasma from baseline were analyzed in a clinical study which is described in more detail below (see the Methods section of this example).

Using a Luminex bead-based immunoassay, plasma leptin levels were determined in 80 samples obtained on Day −1 pre-treatment and Day 3-post treatment from 40 healthy subjects receiving CD24Fc or placebo. The data are summarized in Table 1.

TABLE 1

Leptin levels in subject plasma.

| Subject # | Cohort | Sample Day | Replicate 1: Leptin, pg/ml | Replicate 2: Leptin, pg/ml | Average: Leptin, pg/ml |
|---|---|---|---|---|---|
| 002 | Placebo | Day −1 | 2057.5 | 2151.1 | 2104.3 |
| 002 | Placebo | Day 3 | 3101.0 | 2603.7 | 2852.4 |
| 003 | 10 mg | Day −1 | 8764.2 | 7524.7 | 8144.4 |
| 003 | 10 mg | Day 3 | 10738.8 | 9318.1 | 10028.4 |
| 006 | 10 mg | Day −1 | 3205.3 | 3461.2 | 3333.2 |
| 006 | 10 mg | Day 3 | 4919.7 | 5651.1 | 5285.4 |
| 009 | 10 mg | Day −1 | 26019.6 | 33582.9 | 29801.2 |
| 009 | 10 mg | Day 3 | 25430.8 | 26998.1 | 26214.4 |
| 010 | 10 mg | Day −1 | 3657.9 | 3961.1 | 3809.5 |

TABLE 1-continued

Leptin levels in subject plasma.

| Subject # | Cohort | Sample Day | Replicate 1: Leptin, pg/ml | Replicate 2: Leptin, pg/ml | Average: Leptin, pg/ml |
|---|---|---|---|---|---|
| 010 | 10 mg | Day 3 | 4705.2 | 5613.2 | 5159.2 |
| 008 | 10 mg | Day -1 | 4055.9 | 4856.4 | 4456.2 |
| 008 | 10 mg | Day 3 | 11582.4 | 14660.8 | 13121.6 |
| 012 | Placebo | Day -1 | 12345.2 | 14724.4 | 13534.8 |
| 012 | Placebo | Day 3 | 14293.5 | 17111.0 | 15702.3 |
| 016 | 10 mg | Day -1 | 5281.3 | 6345.6 | 5813.4 |
| 016 | 10 mg | Day 3 | 5562.1 | 5491.4 | 5526.7 |
| 033 | 30 mg | Day -1 | 7906.4 | 8295.2 | 8100.8 |
| 033 | 30 mg | Day 3 | 15080.8 | 15884.3 | 15482.5 |
| 042 | Placebo | Day -1 | 3795.8 | 4013.6 | 3904.7 |
| 042 | Placebo | Day 3 | 4153.9 | 4767.0 | 4460.4 |
| 047 | 30 mg | Day -1 | 11751.1 | 13536.1 | 12643.6 |
| 047 | 30 mg | Day 3 | 14161.9 | 16374.2 | 15268.1 |
| 052 | Placebo | Day -1 | 4022.3 | 4668.0 | 4345.2 |
| 052 | Placebo | Day 3 | 5699.2 | 6002.9 | 5851.0 |
| 060 | 30 mg | Day -1 | 13672.4 | 16908.8 | 15290.6 |
| 060 | 30 mg | Day 3 | 18703.5 | 19928.7 | 19316.1 |
| 063 | 30 mg | Day -1 | 6375.7 | 7636.9 | 7006.3 |
| 063 | 30 mg | Day 3 | 8173.2 | 9556.2 | 8864.7 |
| 066 | 30 mg | Day -1 | 15790.3 | 17753.7 | 16772.0 |
| 066 | 30 mg | Day 3 | 24460.6 | 27606.1 | 26033.3 |
| 067 | 30 mg | Day -1 | 2141.7 | 1618.8 | 1880.2 |
| 067 | 30 mg | Day 3 | 1908.2 | 1721.9 | 1815.0 |
| 088 | Placebo | Day -1 | 2389.5 | 1932.3 | 2160.9 |
| 088 | Placebo | Day 3 | 2273.8 | 2305.3 | 2289.6 |
| 090 | 60 mg | Day -1 | 4883.8 | 4147.8 | 4515.8 |
| 090 | 60 mg | Day 3 | 4884.7 | 4864.1 | 4874.4 |
| 096 | 60 mg | Day -1 | 6991.8 | 6135.6 | 6563.7 |
| 096 | 60 mg | Day 3 | 9448.9 | 8672.7 | 9060.8 |
| 105 | 60 mg | Day -1 | 21867.1 | 20502.8 | 21185.0 |
| 105 | 60 mg | Day 3 | 27647.6 | 28394.9 | 28021.2 |
| 124 | Placebo | Day -1 | 787.0 | 811.4 | 799.2 |
| 124 | Placebo | Day 3 | 1038.7 | 1140.8 | 1089.8 |
| 129 | 60 mg | Day -1 | 10978.2 | 12103.2 | 11540.7 |
| 129 | 60 mg | Day 3 | 12475.3 | 15487.5 | 13981.4 |
| 130 | 60 mg | Day -1 | 10948.9 | 13845.4 | 12397.2 |
| 130 | 60 mg | Day 3 | 14237.8 | 18069.0 | 16153.4 |
| 131 | 60 mg | Day -1 | 7087.5 | 9026.8 | 8057.1 |
| 131 | 60 mg | Day 3 | 7537.5 | 9046.6 | 8292.1 |
| 134 | 120 mg | Day -1 | 27893.0 | 31498.7 | 29695.9 |
| 134 | 120 mg | Day 3 | 38629.1 | 43787.4 | 41208.2 |
| 149 | Placebo | Day -1 | 494.4 | 386.1 | 440.3 |
| 149 | Placebo | Day 3 | 740.8 | 650.8 | 695.8 |
| 143 | Placebo | Day -1 | 11114.0 | 9806.6 | 10460.3 |
| 143 | Placebo | Day 3 | 13506.2 | 10982.0 | 12244.1 |
| 147 | 120 mg | Day -1 | 7143.4 | 5834.3 | 6488.8 |
| 147 | 120 mg | Day 3 | 10558.2 | 8223.6 | 9390.9 |
| 148 | 120 mg | Day -1 | 1830.8 | 1432.5 | 1631.7 |
| 148 | 120 mg | Day 3 | 2193.1 | 1930.4 | 2061.7 |
| 157 | 120 mg | Day -1 | 884.3 | 781.7 | 833.0 |
| 157 | 120 mg | Day 3 | 1224.7 | 1087.3 | 1156.0 |
| 161 | 120 mg | Day -1 | 6576.9 | 5863.6 | 6220.3 |
| 161 | 120 mg | Day 3 | 8689.1 | 7117.7 | 7903.4 |
| 171 | 120 mg | Day -1 | 2899.6 | 2606.4 | 2753.0 |
| 171 | 120 mg | Day 3 | 2872.4 | 2592.9 | 2732.6 |
| 181 | Placebo | Day -1 | 2433.6 | 2206.1 | 2319.8 |
| 181 | Placebo | Day 3 | 2384.8 | 2171.0 | 2277.9 |
| 212 | Placebo | Day -1 | 6780.4 | 6600.6 | 6690.5 |
| 212 | Placebo | Day 3 | 10183.2 | 9953.6 | 10068.4 |
| 179 | 240 mg | Day -1 | 19575.6 | 20203.2 | 19889.4 |
| 179 | 240 mg | Day 3 | 29443.7 | 30264.3 | 29854.0 |
| 213 | 240 mg | Day -1 | 19.4 | 19.9 | 19.7 |
| 213 | 240 mg | Day 3 | 31.0 | 31.6 | 31.3 |
| 216 | 240 mg | Day -1 | 321.2 | 326.1 | 323.7 |
| 216 | 240 mg | Day 3 | 448.1 | 453.2 | 450.6 |
| 211 | 240 mg | Day -1 | 811.7 | 817.6 | 814.7 |
| 211 | 240 mg | Day 3 | 1883.2 | 1889.4 | 1886.3 |
| 214 | 240 mg | Day -1 | 888.5 | 887.8 | 888.1 |
| 214 | 240 mg | Day 3 | 981.2 | 976.5 | 978.9 |
| 218 | 240 mg | Day -1 | 900.6 | 892.7 | 896.6 |
| 218 | 240 mg | Day 3 | 1831.2 | 1808.1 | 1819.7 |

The analytical sensitivity or limit of detection (LOD) was determined as the value calculated from the standard curve at the point lying 2 standard deviations above the mean background (twenty zero standard replicates). The lower limit of quantification (LLOQ) was determined using a 2-fold dilution series of the standards in standard diluent assayed in triplicate over three different rounds, and is defined as the point at which the coefficient of variation (CV) for the measurement was 30%. The CV was calculated and plotted against concentration, and LLOQ was interpolated from the plot. The assay performance characteristics are as follow in Table 2.

TABLE 2

| Analyte | Leptin |
|---|---|
| Unit | pg/ml |
| LOD | 8.1 |
| LLOQ | 18.2 |
| Standard Curve Range | 7.7-600,000 |

FIG. 2 displays the ratio of leptin on day3/day−1 for patients grouped by dosing cohort. As the figure shows, there is a upward trend in the relative amount circulating leptin following CD24Fc treatment and between the 0, 60, 120 and 240 mg cohorts this increase is statistically significant (P=0.009397, dose-dependent general linear model regression), demonstrating a dose dependent increase above 60 mg. Furthermore, there is a statistically significant increase in the level of leptin following CD24Fc administration in the 240 mg cohort compared to placebo (0 mg) (P=0.05 as determined by Student's T test), indicating that CD24Fc is effective for increasing leptin in human patients.

Methods

This was a Phase I, randomized, double-blind, placebo-controlled, single ascending dose study to assess the safety, tolerability, and PK of CD24Fc in healthy male and female adult subjects. A total of 40 subjects in 5 cohorts of 8 subjects each were enrolled in this study. Six of the 8 subjects in each cohort received study drug and 2 subjects received placebo (0.9% sodium chloride, saline). The first cohort was dosed with 10 mg and succeeding cohorts received 30 mg, 60 mg, 120 mg, and 240 mg of CD24Fc or matching placebo. Dosing was based on a fixed amount of CD24Fc and not based weight or BSA. Subjects were dosed at least 3 weeks apart to allow for review of safety and tolerability data for each prior cohort. Administration of the next higher dose to a new cohort of subjects was permitted only if adequate safety and tolerability had been demonstrated.

In each cohort, the initial 2 subjects were 1 study drug recipient and 1 placebo recipient on Day 1. The 3rd to 5th and 6th to 8th subjects were dosed after Day 7 (a minimum of 24 hours apart between the subgroups). Each subject was dosed at least 1 hour apart in the same subgroup. If necessary, dosing of the rest of subjects was delayed pending review of any significant safety issues that may have arisen during the post-dose period involving the first or second subgroups in that cohort. The subsequent cohort was dosed at least 3 weeks after the prior cohort.

Screening Period: The Screening Visit (Visit 1) occured up to 21 days prior to the beginning of the active treatment period. After providing informed consent, subjects underwent screening procedures for eligibility.

Treatment Period: Subjects were admitted to the Clinical Pharmacology Unit (CPU) on Day −1 (Visit 2), and the randomized treatment period began on Day 1 following a 10-hour minimum overnight fast. Subjects were randomly assigned to treatment with CD24Fc or placebo as a single dose. Subjects remained confined until the morning of Day 4.

Follow-up: All subjects returned to the CPU on Day 7, Day 14, Day 21, Day 28, and Day 42 (±1 day) for follow-up visits (Visit 3, Visit 4, Visit 5, Visit 6, and Visit 7). Visit 7 was the final visit for all subjects.

Duration of Treatment:

The total study duration for each subject was up to 63 days.

Single-dose administration occurred on Day 1.
Number of Subjects:
Planned: 40 subjects
Screened: 224 subjects
Randomized: 40 subjects
Completed: 39 subjects
Discontinued: 1 subject Diagnosis and Main Criteria for Inclusion: The population for this study was healthy males and females between the ages of 18 and 55 years, inclusive, with a body mass index between 18 kg/m² and 30 kg/m², inclusive.

Investigational Product and Comparator Information: CD24Fc: single dose of 10 mg, 30 mg, 60 mg, 120 mg, or 240 mg administered via IV infusion; lot number: 09MM-036. CD24Fc is a fully humanized fusion protein consisting of the extracellular domain of human CD24 and the fragment crystallizable region of human immunoglobulin G1 (IgG1Fc). CD24Fc was supplied as a sterile, clear, colorless, preservative-free, aqueous solution for IV administration. CD24Fc was formulated as single dose injection solution, at a concentration of 10 mg/mL and a pH of 7.2. Each CD24Fc vial contained 160 mg of CD24Fc, 5.3 mg of sodium chloride, 32.6 mg of sodium phosphate dibasic heptahydrate, and 140 mg of sodium phosphate monobasic monohydrate in 16 mL±0.2 mL of CD24Fc. CD24Fc was supplied in clear borosilicate glass vials with chlorobutyl rubber stoppers and aluminum flip-off seals.

Matching placebo (0.9% sodium chloride, saline) administered via IV infusion; lot numbers: P296855, P311852, P300715, P315952.

The intent-to-treat (ITT) Population consisted of all subjects who received at least 1 dose of the study drug. The ITT Population was the primary analysis population for subject information and safety evaluation.

Plasma samples were collected at Day 1 pre-dose, at Day dosing, and at Day 2, Day 3, Day 4, Day 7, Day 14, Day 21 (±1), Day 28 (±1), and Day 42 (±1).

Reference cited: Rodriguez A J, Mastronardi C A, Paz-Filho G J. New advances in the treatment of generalized lipodystrophy: role of metreleptin. Therapeutics and Clinical Risk Management. 2015; 11:1391-1400. doi:10.2147/TCRM.S66521.

The invention claimed is:

1. A method of increasing circulating leptin levels in the bloodstream of a subject, comprising administering a CD24 protein to a subject with reduced leptin levels, wherein the CD24 protein comprises (a) a mature human CD24 polypeptide comprising the sequence set forth in SEQ ID NO: 1 or 2; and, (b) a Fc region of a human IgG protein; wherein the Fc region is fused to the C-terminus of the CD24 protein; and, wherein the administering increases circulating leptin levels in the bloodstream of the subject.

2. The method of claim 1, wherein the subject has lipodystrophy.

3. The method of claim 1, wherein the subject has HIV.

4. The method of claim 1, wherein the subject has received antiviral therapy.

5. The method of claim 1, wherein the Fc region comprises a hinge region and CH2 and CH3 domains of the human IgG protein.

6. The method of claim 5, wherein the human IgG protein is selected from the group consisting of IgG1, IgG2, IgG3, and IgG4.

7. The method of claim 1, wherein the CD24 protein comprises the sequence set forth in SEQ ID NO: 6, 11 or 12.

8. The method of claim 1, wherein the CD24 protein is soluble.

9. The method of claim 1, wherein the CD24 protein is glycosylated.

10. A method of treating or preventing lipodystrophy syndrome in a subject in need thereof, comprising administering a CD24 protein to the subject, wherein the CD24 protein comprises (a) a mature human CD24 polypeptide comprising the sequence set forth in SEQ ID NO: 1 or 2; and, (b) a Fc region of a human IgG protein; and, wherein the Fc region is fused to the C-terminus of the CD24 protein.

11. The method of claim 10, wherein the subject has HIV.

12. The method of claim 10, wherein the subject received antiviral therapy.

13. The method of claim 10, wherein the Fc region comprises a hinge region and CH2 and CH3 domains of the human IgG protein.

14. The method of claim 13, wherein the human IgG protein is selected from the group consisting of IgG1, IgG2, IgG3, and IgG4.

15. The method of claim 10, wherein the CD24 protein comprises the sequence set forth in SEQ ID NO: 6, 11 or 12.

16. The method of claim 10, wherein the CD24 protein is soluble.

17. The method of claim 10, wherein the CD24 protein is glycosylated.

18. The method of claim 7, wherein the amino acid sequence of the CD24 protein consists of the sequence set forth in SEQ ID NO: 6, 11 or 12.

19. The method of claim 15, wherein the amino acid sequence of the CD24 protein consists of the sequence set forth in SEQ ID NO: 6, 11 or 12.

* * * * *